United States Patent [19]

Cochran

[11] Patent Number: 4,731,731

[45] Date of Patent: Mar. 15, 1988

[54] DIALYSIS MACHINE HAVING ENHANCED D/A RESOLUTION

[76] Inventor: Michael J. Cochran, 16178 Greenwood Rd., Monte Sereno, Calif. 95030

[21] Appl. No.: 704,049

[22] Filed: Feb. 21, 1985

[51] Int. Cl.[4] .................... G06G 7/57; H03M 1/18; B01D 13/00

[52] U.S. Cl. ................................ 364/510; 210/321.3; 340/347 AD; 340/347 CC; 340/347 M; 364/557; 364/558

[58] Field of Search ............... 364/510, 550, 557, 558, 364/571; 210/96.2, 135, 137, 197, 321.2, 321.3; 340/347 M, 347 DA, 347 CC; 128/630, DIG. 13; 324/442, 445; 73/600

[56] References Cited

U.S. PATENT DOCUMENTS

| | | | |
|---|---|---|---|
| 3,878,095 | 4/1975 | Frasier et al. | 210/321.3 |
| 4,060,485 | 11/1977 | Eaton | 210/321.3 |
| 4,153,554 | 5/1979 | von der Heide et al. | 210/321.3 |
| 4,366,051 | 12/1982 | Fischel | 210/96.2 |
| 4,447,803 | 5/1984 | Crosby et al. | 340/347 AD |
| 4,601,830 | 7/1986 | Chen | 210/321.3 |

OTHER PUBLICATIONS

Federal Scientific Corp.; FSC-L-569/100; "Dithering Increases Dynamic Range and Improves Linearity"; 8/24/73.

Primary Examiner—Parshotam S. Lall
Assistant Examiner—Kevin J. Teska

[57] ABSTRACT

A dialysis machine has control circuit which detects changes in input water temperature and compensates the water heater. The control circuit detects changes in the conductivity of the dialysate concentrate and compensates the concentrate pump. Changes in supply voltage are detected and the outputs of the several sensors and the inputs to the pumps and heater compensated. The control circuit periodically calibrates the blood leak detector. In each of the feedback loops which service the heater and each of the pumps, the control circuit varies both the loop response time and the loop gain to compensate for changes in the dialysate flow rate. The resolution of the D/A converters which drive the pumps are enhanced by the control circuit by time modulating the LSB of the respective digital drive value. If any of the several sensed operating conditions varies significantly from the expected value, the control circuit terminates dialysis.

8 Claims, 10 Drawing Figures

DIALYSIS MACHINE HAVING ENHANCED D/A RESOLUTION

CROSS REFERENCE TO RELATED APPLICATIONS

Related subject matter is disclosed in the following applications, all invented by Michael J. Cochran and filed simultaneously herewith:

1. U.S. application Ser. No. 704,054, entitled A DIALYSIS MACHINE WHICH ANTICIPATES TEMPERATURE CHANGES.
2. U.S. application Ser. No. 704,053, entitled A DIALYSIS MACHINE WHICH ANTICIPATES CONCENTRATION CHANGES.
3. U.S. application Ser. No. 704,051, entitled A DIALYSIS MACHINE WHICH ANTICIPATES FLOWRATE CHANGES.
4. U.S. application Ser. No. 704,058, entitled A DIALYSIS MACHINE HAVING SELF-CALIBRATED BLOOD LEAK DETECTOR.
5. U.S. application Ser. No. 704,059, entitled A DIALYSIS MACHINE HAVING VARIABLE LOOP GAIN.
6. U.S. application Ser. No. 704,052, entitled A DIALYSIS MACHINE WHICH VERIFIES OPERATING PARAMETERS.

FIELD OF THE INVENTION

The present invention relates generally to a dialysis machine, and, more particularly, to a dialysis machine having a controller which provides enhances D/A resolution.

BACKGROUND OF THE INVENTION

Artificial kidney systems generally consist of several major components, some of which are used only once and others of which are used repeatedly. Typically, the artificial kidney itself is used only once and then discarded, together with all related tubing, needle assemblies, integral tubing clamps, injection ports and the like. Likewise, after passing through the artificial kidney, the spent dialysate solution is discharged into a suitable waste disposal system. In contrast, the dialysis machine, blood pump and anticoagulent injection pump are reused, each being appropriately cleaned between treatments. In addition to these patient-specific components, the dialysis treatment center typically includes a suitably-sized water conditioning system, usually of the reverse osmosis (RO) or deionization/reionization type. Convenient access must also be provided to a source of dialysate concentrate appropriate for the machine and the patient. Depending upon the design of the dialysis machine, provision may also be necessary for returning excess dialysate concentrate to the supply source.

Although the exact sequence varies with the particular type of dialysis machine, preparation for a typical treatment usually begins by flushing an appropriate sanitizing solution such as formaldehyde through all of the internal fluid passages of the machine. At the end of a suitable sanitizing time period, the sterilant is then purged from the machine, typically using the conditioned water. The machine can then be coupled to the source of dialysate concentrate and priming initiated.

During the priming operation, the dialysis machine proceeds to produce dialysate in accordance with several parameters set by the operator via input switches, dials and the like. Typically, these parameters include the temperature at which the dialysate is to be delivered to the artificial kidney, the rate at which the dialysate is to be delivered, and the pressure at which the dialysate is to be delivered. In the priming mode, however, the dialysate being produced is either internally or externally recirculated so as to bypass the artificial kidney. Once the dialysis machine determines that the dialysate is being produced at the selected temperature, flow rate and pressure, the operator may be notified that dialysis may be commenced.

While the dialysis machine is stabilizing, the operator may be preparing the patient by coupling the blood tubing assembly between the patient and the artificial kidney, with an appropriate portion thereof installed in the associated blood pump. Typically, an infusion pump is also coupled to the blood tubing and adjusted to provide a controlled rate of injection of a suitable anticoagulent such as heparin. In most systems, venous and arterial pressure monitors are also coupled to the blood tubing assemble so that dangerous pressure levels may be detected before the patient is injured.

Once the machine is primed and the patient fully prepared, the operator will enable the dialysis machine to circulate the conditioned dialysate through the artificial kidney, while maintaining a selected negative transmembrane pressure within the artificial kidney so that excess fluids may be removed from the patient's blood. Typically, while operating in this dialyze mode, the dialysis machine continues to monitor the temperature, flow rate, concentration and pressure of the dialysate delivered to the artificial kidney. If any of these parameters deviates beyond the capability of the machine to correct, the dialysis machine will sound an alarm and immediately terminate delivery of the dialysate. In the event of such a shutdown, operator intervention is required before the dialysis machine will resume delivery of the dialysate.

One of the more automatic and in genereall safest of the type of dialysis machine just described is that shown and described in U.S. Pat. No. 4,153,554. However, the performance of the latter machine was limited in several areas. One primary source of limitation was the response delay inherent in the several servoloops within the control system. For example, due to the large size of the water heater used to heat the conditioned supply water to the desired delivery temperature, the lag time between a sensed temperature deviation and actual sensed response was significant. This problem was exacerabated by variations in the temperature of the supply water as well as changes in the flow rate of the water through the heating chamber. In general, the reservoir approach used to compensate for this problem was only partially successful.

One other major source of performance limitation in this earlier system was the type of sensors used to sense such parameters as the temperature of the conditioned water and the conductivity of the dialysate. Since these sensors were electrically powered, variations in the supply voltage could result in different readings although the sensed parameter in fact had not changed. However, because the control circuit was unable to distinguish between the causes of the sensed deviations, corrective actions were set in motion which were not only unnecessary but also disruptive in and of themselves. Again, the averaging approach used therein to compensate for instantaneous variations in supply voltage were only partially successful, particularly since relatively long term voltage drift is not at all uncommon in many areas. In addition, this introduced further delay in the response loop.

Another aspect of this same problem related to the variation of the pump speeds due to variations in supply voltage. Even though the dialysate concentrate supply side of the manifold system was ratioed so that both the water and the dialysate concentrate pumps could be driven at the same speed to maintain consistent concentration, the overall dialysate delivery rate still varied as a result of the variation in operating speed of both pumps.

SUMMARY OF THE INVENTION

Accordingly, it is an object of the present invention to provide an improved dialysis machine having a control circuit which artivicially enhances the resolution of the D/A converters used to drive certain components of the dialysis machine.

Another object of the present invention is to provide a dialysis machine having an improved control circuit which can artificially enhance the resolution of the D/A converters used in the dialysis machine by selectively time modulating the least significant bit of the digital values input to such D/A's.

These and other objects are achieved in a dialysis machine comprising one or more pumps which cooperate to supply dialysate at a rate proportional to an analog supply rate signal, and a flow rate control circuit which provides the analog supply rate signal to the pump(s), the analog supply rate signal having a value proportional to the value of a digital flow rate signal having a first predetermined number of bits of resolution. In accordance with the present invention, the dialysis machine includes resolution enhancement logic which is responsive to a digital flow rate control signal having a second predetermined number of bits of resolution, with the second predetermined number being at least one bit greater than the first predetermined number. During the operation of the dialysis machine, the resolution enhancement logic varies the value of the least significant bit of the digital flow rate signal during a selected resolution period in proportion to the value of the least significant bit of the digital flow rate control signal. In the preferred embodiment, the dialysis machine includes a water supply pump, a concentrate supply pump and a negative pressure pump, and corresponding flow rate control circuits which provide respective analog supply rate signals in proportion to the value of respective digital flow rate signals. In this form, the resolution enhancement logic varies the value of the least significant bit of each of the digital flow rate signals during the selected resolution period in proportion to the value of the least significant bit of respective digital flow rate control signals. If the resolution of the digital flow rate control signal is greater than the resolution of the digital flow rate signal by a plurality of less significant bits, the resolution enhancement logic varies the value of the least significant bit of the digital flow rate signal during the selected resolution period in proportion to the combined binary value of the plurality of less significant bits of the digital flow rate control signal.

BEST MODE FOR CARRYING OUT THE INVENTION

Figure 1:
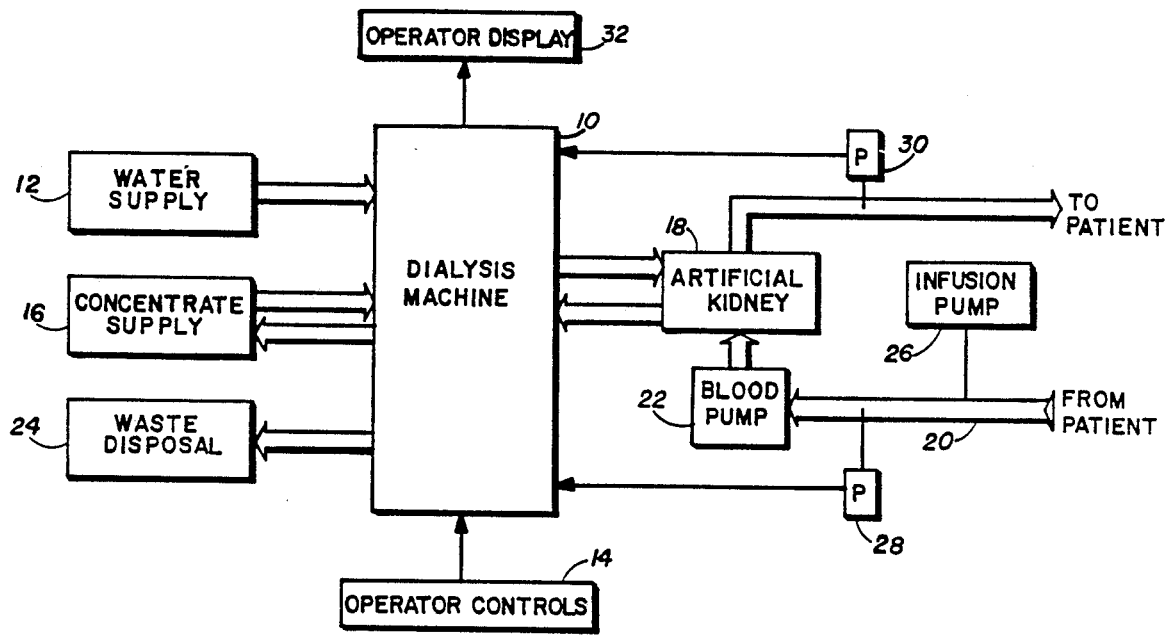
FIG. 1 is a block representation of a dialysis machine in accordance with the preferred embodiment of the present invention.

Shown in FIG. 1 is a dialysis machine 10 configured in the dialyze mode. In this mode, the dialysis machine draws conditioned water from a suitable water supply 12 at a rate related to a delivery rate selected by an operator (not shown) via a set of operator controls 14. This supply water is then heated by the dialysis machine 10 to a temperature related to a delivery temperature selected by the operator via the operator controls 14. From a suitable dialysate concentrate supply 16, the dialysis machine draws the concentrate at a rate proportional to the water supply rate, returning excess concentrate to the concentrate supply 16 as necessary. The concentrate is then mixed with the heated water at a precise 34 to 1 ratio. The resultant dialysate is then delivered to an artificial kidney 18 which has been coupled to a patient (not shown) via a conventional tubing harness 20. Blood drawn from the patient's arterial system is circulated by a conventional blood pump 22 through the artificial kidney 18 and returned to the patient's venous system. The spent dialysate is removed from the artificial kidney 18 by the dialysate machine 10 at a somewhate greater rate than the delivery rate so that an operator-selected transmembrane pressure may be maintained within the artificial kidney 18. In this manner, excess fluids maybe removed from the patient's bloodstream. The spent dialysate containing the extracted wastes and excess fluids is then discharged into a suibable waste disposal system 24.

To prevent blood coagulation in the artifical kidney 18, an infusion pump 26 injects a suitable anticoagulant such as heparin at an operatore-selected rate into the arterial side of the tubing harness 20. The patient's arterial and venous pressures are constantly monitored by the dialysis machine 10 via respective pressure transducers 28 and 30. Each of these pressures is constantly reported by the dialysis machine 10 via an operator display 32. In a similar manner, the operator display 32 constantly reports the temperature and conductivity of the delivered dialysate, the latter being a measure of the concentration of the delivered dialysate. Any deviation outside of respective ranges set by the operator via the operator controls 14 will cause an alarm to sound and dialysis to cease.

Figure 2:
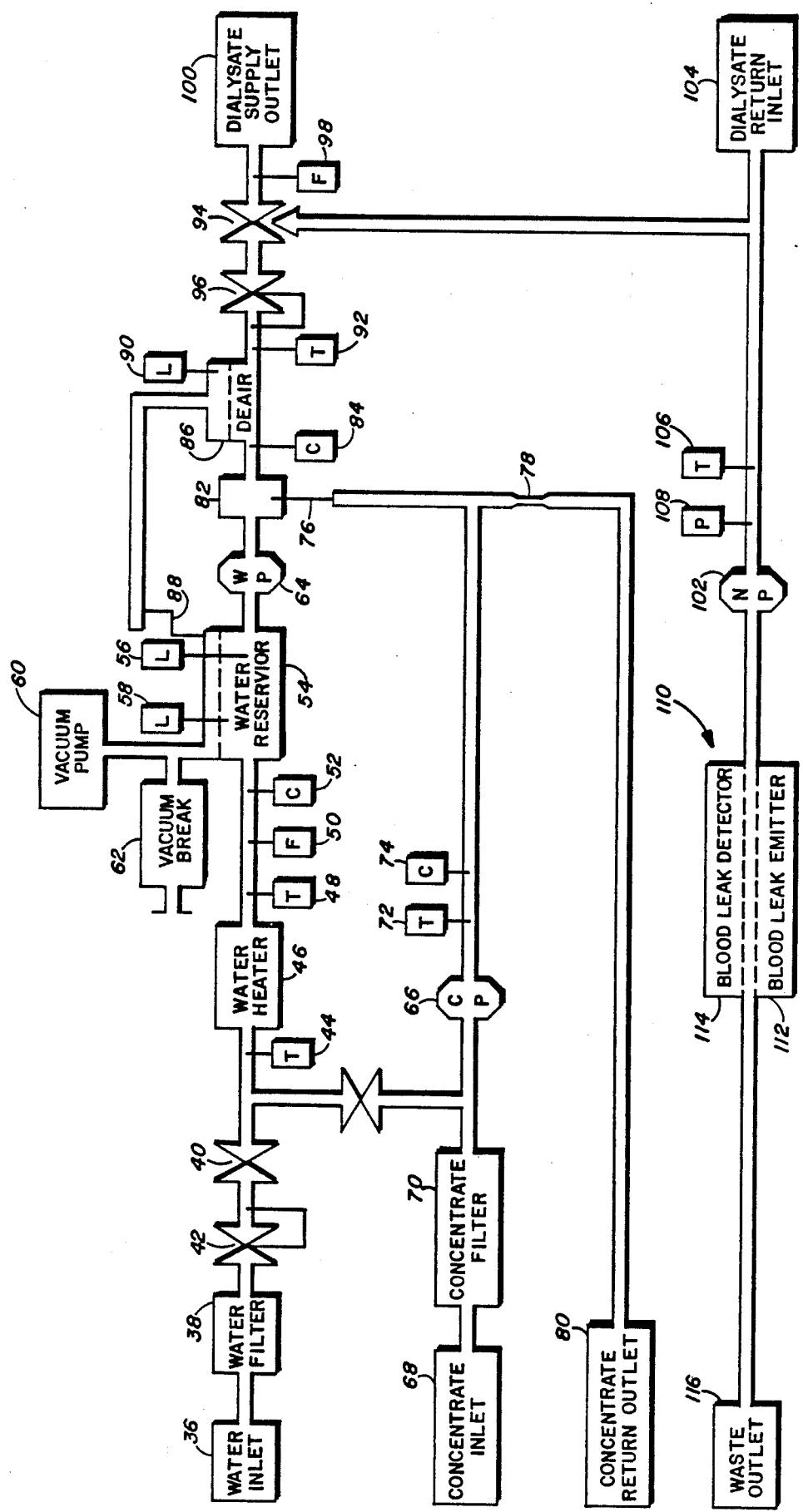
FIG. 2 is a block representation of the hydraulics circuit of the dialysis machine of FIG. 1.

Shown in FIG. 2 is the hydraulic circuit 34 of the dialysis machine 10. In the hydraulic circuit 34, supply water from the water supply 12 (see FIG. 1) flows through a water inlet 36 and a suitable water filter 38 in response to the actuation of a water inlet valve 40. A pressure regulator 42 is also provided to regulate the inlet water pressure to a suitably low level on the order of about 10 psi. In the preferred form, the pressure regulator 42 is provided on theinlet side of the water inlet valve 40 so that the latter need not be sized to withstand the full pressure present at the water inlet 36.

From the water inlet valve 40, the supply water flows past a temperature feed forward sensor 44 into a water heater 46. From the water heater 46, the heated water flows past a temperature feedback sensor 48, a water flow rate sensor 50 and a water conductivity cell 52 into a water reservoir 54. Within the water reservoir 54, lower and upper level sensors 56 and 58, respectively, monitor the water level and assist in controlling the water inlet valve 40. To eliminate any gases which may be released from the heated water, a vacuum pump 60 maintains a partial vacuum on the order of about 5 inches of mercury below ambient above the level of the water within the reservoir 54. In the preferred form, a vacuum breaker 62 is also provided to prevent the vacuum from exceeding about 8 inches of mercury. From the water reservoir 54, the heated water is drawn by a water supply pump 64 at a rate sufficiently below the operator-selected delivery rate to compensate for the quantity of concentrate which must be added to produce the delivered dialysate.

Meanwhile, a concentrate supply pump 66 is drawing dialysate concentrate from the concentrate supply 16 (see FIG. 1) through a dialysate inlet 68 and a dialysate filter 70 at substantially the same rate as the water supply pump 64 is drawing heated water from the reservoir 54. From the concentrate supply pump 66, the concentrate flows past a concentrate temperature sensor 72 and a concentrate conductivity sensor 74 to a flow divider comprised of a concentrate injection orifice 76 and a concentrate return orifice 78. All of the concentrate which passes through the return orifice 78 is returned to the concentrate supply 16 (see FIG. 1) via a concentrate return outlet 80, while the portion of the concentrate which passes through the injection orifice 76 is mixed with the heated water provided by the water supply pump 64 in a mixing chamber 82. In the preferred form, the return orifice 78 has an internal diameter of one-sixteenth (1/16th) of an inch and the injection orifice 76 is a twenty (20) gauge hypodermic needle to provide a return-to-injection ratio on the order of 7-to-1. However, due to the high viscosity of the concentrate, the effective ratio is of the order of about 34-to-1, the preferred dialysate mixing ratio.

From the mixing chamber 82, the dialysate flows past a dialysate conductivity sensor 84 into a de-air chamber 86 where any residual gases which may be released from the dialysate is drawn off and returned to the reservoir 54 via a gas return orifice 88. A level sensor 90 monitors the water level in the de-air chamber 86. From the de-air chamber 86, the dialysate flows past a dialysate temperature sensor 92 to a bypass valve 94. In the preferred form, a back pressure regulator 96 is provided on the inlet side of the bypass valve 94 to maintian a substantially constant pressure on the order of about 4 psi concentrate supply pump 66. As long as the dialysis machine 10 is in the dialyze mode, the bypass valve 94 allows the dialysate to flow past a dialysate flow sensor 98 to a dialysate supply outlet 100 for delivery to the atificial kidney 18 as shown in FIG. 1.

From the artificial kidney 18 (see FIG. 1), the spent dialysate is drawn off by a negative pressure pump 102 at a rate which is sufficient to maintain the operator-selected transmembrane pressure within the artificial kidney 18. As the spent dialysate returns via a dialysate return inlet 104, it flows past a dialysate return temperature sensor 106 and a negative pressure transducer 108. From the negative pressure pump 102, the spent dialysate flows through a blood leak detector 110 comprising a light emitter 112 and a ligher detector 114. The spent dialysate is then discharged via a waste outlet 116 into the waste disposal system 24 (see FIG. 1).

Figure 3:
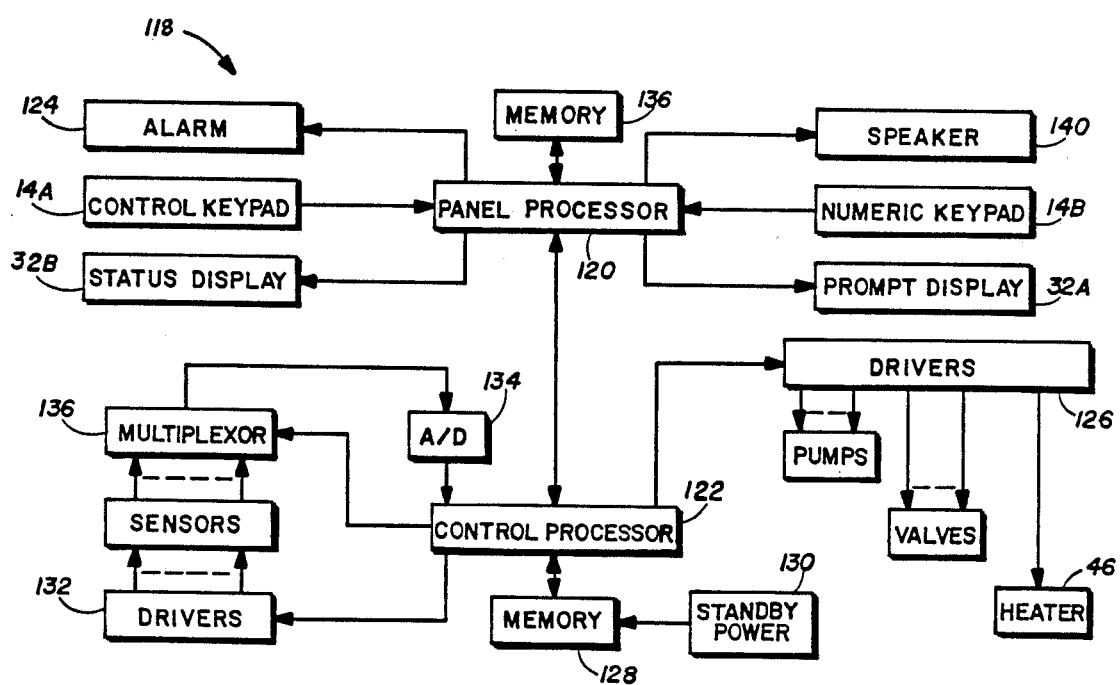
FIG. 3 is a schematic representation of the control circuit of the dialysis machine of FIG. 1.

Shown in FIG. 3 is a block diagram of the control circuit 118 for the dialysis machine 10. In the illustrated form, the processing activity is shared between a panel processor 120 and a control processor 122. In general, the panel processor 118 is responsible for maintaining communication with the operator, while the control processsor 122 is responsible for maintaining the operation of the dialysis machine 10 within the parameters established by the operator for the selected mode of operation.

Upon power up, the panel processor 120 will execute a self-test to determine that the control circuitry 118 is functional. If an error is found, the panel processor 120 will sound an alram 124 and provide an error message on a prompt display 32A. If no error is found, the panel processor 120 will advise the operator via the prompt display 32A that the dialysis machine 10 is entering the rinse mode, and that the concentrate inlet 68 should be connected to the water supply 12 and that the concentrate return outlet 80 should be connected to the waste disposal system 24. When the operator indicates via a control keypad 14A that these connections have been made, the panel processor 120 commands the control processor 122 to enter the rinse mode.

In the rinse mode, the control processor 122 will first activate the several valves and pumps in the hydarulic circuit 34 via respective drivers 126, to drain and refill the flow channels in the hydarulic circuit 34 (see FIG. 2) several times with supply water to eliminate most of the sterilant from the circuit 34. The control processor 122 will then circulate water through the circuit 34 at varying pressure and flow rate to forcefully flush the balance of teh sterilant from the circuit 34. At the end of this rinse sequency, the control processor 122 will deactivate the valves and pumps, and then signal the panel processor 120.

At the end of the rinse mode, the panel processor 120 will prompt the operator to perform a chamical check for residual sterilant, and then wait for the operator to indicate the result. If the operator indicates that sterilant is still present, the panel processor 120 commands the control processor 122 to repeat the rinse sequence. If the operator indicates that no sterilant is present, the panel processor 120 will prompt the operatore to reconnect the concentrate inlet 68 to the concentrate supply 16. Upon the operator indicataing that this connection has been made, the panel processor 120 commands the control processor 122 to prime the concentrate lines in the circuit 34. When the control processor 122 acknowledges that the system is primed, the panel processor 120 will prompt the operator to reconnect the concentrate return outlet 80 to the concentrate supply 16. Upon the operator indicating that this connection has been made, the panel processor 120 will command the control processor 122 to enter the by-pass mode.

In the bypass mode, the control processor 122 will initiate production of dialysate using default conductivity, temperature and flow rate parameters stored in a portion of a memory 128 provided with a standby power supply 130. However, the control processor 122 will position the bypass valve 94 in the bypass position so that all of the dialysate will be recirculated within the circuit 34. During dialysate production, the control processor 122 activates the several temperature, conductivity and flow sensors via respective drivers 132, and monitors the several sensed parameters using an analog-to-digital converter (A/D) 134 which is coupled to the sensors via a multiplexor 136. As the sensed parameters change, the control processor 122 will update a current conditions table within the memory 128 with the current operating conditions of the circuit 34. Simultaneously, the control processor 122 will update a similar tablwithin a memory 138 of the panel processor 120. Once the control processor 122 determines that the dialysate being produced is within the default parameters, the panel processor 120 will be notified that the system is prepared for dialysis.

As the information in the current conditions table is being updated by the control processor 122, the panel processor 120 will be continuously displaying the current temperature and conductivity of the dialysate being produced using a status display 32B. Upon being notified by the control processor 122 that the dialysis machine 10 is operating within the default parameters, the panel processor 120 will prompt the operator to either confirm or change the default conductivity, temperature and flow rate.

After providing each prompt, the panel processor 120 will scan the control keypad 14A and a numeric keypad 14B for the operator response. If any entry is inappropriate or outside conventional limits, the panel processor 120 will activate a speaker 140 to chastize the operator and then reprompt on the prompt display 32A. If a response is acceptable, the panel processor 120 will store the respective parameter into a desired conditions table in the memory 138. Simultaneously, the panel processor 120 will update a similar table within the memory 128 of the control processor 122. After all parameters have been confirmed or changed, the panel processor 120 will await notification from the control processor 122 that the system has been stabilized to the desired conditions.

Figure 4:
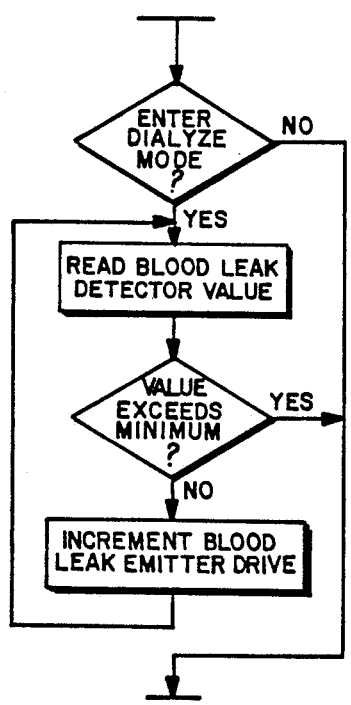
FIG. 4 is a flow diagram of the blood leak detector calibration routine periodically executed by the control processor in the control circuit of FIG. 3.

Upon stabilization, the panel processor 120 will warn the operatore that he dialysis machine 10 is preparing to enter the run mode. If, after a brief pause, the operator has not intervened, the panel processor 120 will request the control processor 122 to enter the run mode. At this time, the control processor 122 will calibrate the blood leak detector 110. As in U.S. Pat. No. 4,153,554, the blood leak detector 110 is constructed so that the light emitter 112 emits a beam of light through at least a portion of the spent dialysate. In response to receiving some of this light, the light detector 114 provides a light detection signal the value of which is proportional to the strength of the light received. So long as the spent dialysate contains no blood, most of the emitted light will be detected and the light detection signal will have a relatively high value. If the spent dialysate contains blood, the proportion of the emitted light actually reaching the light detector 114 will be significantly reduced. Thus, a blood leak may be readily detected by monitoring the light detection signal to determine when the value drops below a selected minimum value. As explained in U.S. Pat. No. 4,153,554, the operation of the blood leak detector 110 is subject to degradation through the accumulation of films on the dialysate side of the lenses of the light emitter 112 and light detector 114. I addition, the sensitivity of the blood leak detector 110 to one type of dialysate may be quite different to another type of dialysate. In the preferred embodiment, however, the control processor 122 automatically compensates for such sources of error as shown in FIG. 4. Recall that in the bypass mode, no dialysate is being circulated through the artificial kidney 18.Thus, the spent dialysate passing through the blood leak detector 110 is known to contain no blood. The control processor 122 is therefore able to calibrate the blood leak detector 110 before entering the dialyze mode, by varying the value of the emitter drive signal used to power the light emitter 112 appropriately until the output of the light detector 114 exceeds the selected minimum value by some suitable operating margin. After the calibration is complete, the control processor 122 will enter the run mode by positioning the bypass valve 94 so that the dialysate is circulated through the artificial kidney 18.

In the run mode, the panel processor 120 will continuously monitor all current conditions, except negative pressure, against the desired conditions, and will sound the alarm 124 upon detecting a deviation beyond established limits. If all current conditions are initially found to be satisfactory, the panel processor 120 will prompt the operator to connect the dialysate supply outlet 100 and the dialysate return inlet 104 to the artificial kidney 18 and to prime the tubing harness 20 with appropriate saline solution. At this time, the panel processor 120 will also request the control processor 122 to provide power to the blood pump 22 and the infusion pump 26. After prompting the operator to perform a chemical check for residual contaminants in the artificial kidney 18 and the various fluid lines, the panel processor 120 will warn the operator that, although the dialysate machine 10 is ready for the patient, the pressure alarms will no be activated until after the ultrafiltration information has been entered.

Using a series of prompts, the panel processor 120 will elicit from the operatore sufficient information to determine the volume of fluids, if any, which must be removed from the patient during the dialysis session. In the preferred form, the panel processor 120 first prompts the operator to enter the ultrafiltration coefficient of the particular artificial kidney 18 being used, and the time period that the patient is to be dialyzed. Using this information, the panel processor 120 calculates the minimum and maximum fluid withdrawal limits of the dialysis machine 10, and then prompts the operator to select a volume within these limits. Provided that the selected volume is within such limits, the panel processor 120 the calculates the transmembrane pressure (TMP) which must be maintained within the artificial kidney 18, by dividing the selected fluid volume by the product of the ultrafiltration coefficient and the dialysis time period. The panel processor 120 stores this TMP parameter in the two desired conditions tables and then requests the control processor 122 to enter the dialyze mode.

At any time while the system is in the dialyze mode, the operator can query the panel processor 120 as to the several operating parameters and the respective limits, if any, and, if appropriate, can request that they be changed. All such changes which are acceptable are then entered by the panel processor 120 into the respective locations in the two desired conditions tables.

In the dialyze mode, the control processor 122 will continually scan each of the sensors and report the current conditions to the panel processor 120 for error anaylysis. Periodically, the control processor 122 will recalculate the necessary operating levels of the heater 46, the supply pump 64 and the concentrate pump 66. Similarly, the control processor 122 periodically recalculates the negative pressure which the negative pressure pump 102 must develop within the artificial kidney 18, by adding the venous pressure sensed by the sensor 30 to the TMP calculated by the panel processor 120.

If, during dialysis, a condition exceeds the limits set for that condition, the panel processor 120 will command the control processor 122 to enter the bypass mode. In response, the control processor 122 will terminate power to the blood pump 22 and the infusion pump 26, and position the bypass valve 94 so that no dialysate will be circulated through the artificial kidney 18. In some cases, such as if a blood leak is detected, the panel processor 120 will command the control processor 122 to enter the run mode. In response, the control processor 122 wil continue to provide dialysate to the artificial kidney 18, but will terminate power to the blood and infusion pumps 22 and 26, respectively. If the error condition is corrected, either by operator intervention or corrective action by the control processor 122, the panel processor 120 will command the control processor 122 to reenter the dialyze mode. Under certain circumstances, such as a moderate pressure error, the operator can request the panel processor 120 to command the control processor 122 to enter the run mode. In response, the panel processor 120 will cease to monitor pressure and command the control processor 122 to enter the run mode. However, if a series error is not corrected by the efforts of the operator and the control processor 122 or if the operator so requests, the panel processor 120 will command the control processor 122 to enter the standby mode. In response, the control processor 122 will shut down the circuit 34.

At the normal termination of the dialysis period, the panel processor 120 will command the control processor 122 to enter the bypass mode. The panel processor 120 then prompts the operator as to the next operation. If the operator indicates that the same patient is to receive more dialysis, the panel processor 120 will cycle the control processor 122 through the run and dialyze modes as described above.

If the operator indicates that another patient is to be dialyzed, the panel processor 120 prompts the operator as to the necessity to sanitize the circuit 34. If the operator responds affirmatively, the panel processor 120 will request the operator to connect the concentrate inlet 68 to the sterilant source (not shown) and the concentrate return outlet 80 to the water inlet 36. AFter the operator has done so, the panel processor 120 commands the control processor 122 to enter the sanitize mode. In response, the control processor 122 will circulate the sterilant throughout all of the flow paths of the circuit 34 for a suitable sanitizing time period. If, after the circuit 34 has been sanitized, the operator indicates that another patient will not be available for dialysis until later, the panel processor 120 will command the control processor 122 to enter the standby mode. When the operator indicates that the new patient is ready, the panel processor 120 then cycles the control processor 122 through the rinse, bypass, run and dialyze modes as described above.

If the operator indicates that no patient is to be dialyzed, the panel processor 120 cooperates with the operator to sanitize and/or rinse the circuit 34 before commanding the control processor 122 to shut down the circuit 34. The panel processor 120 then prompts the operator to turn off the dialysis machine 10.

Figure 5:
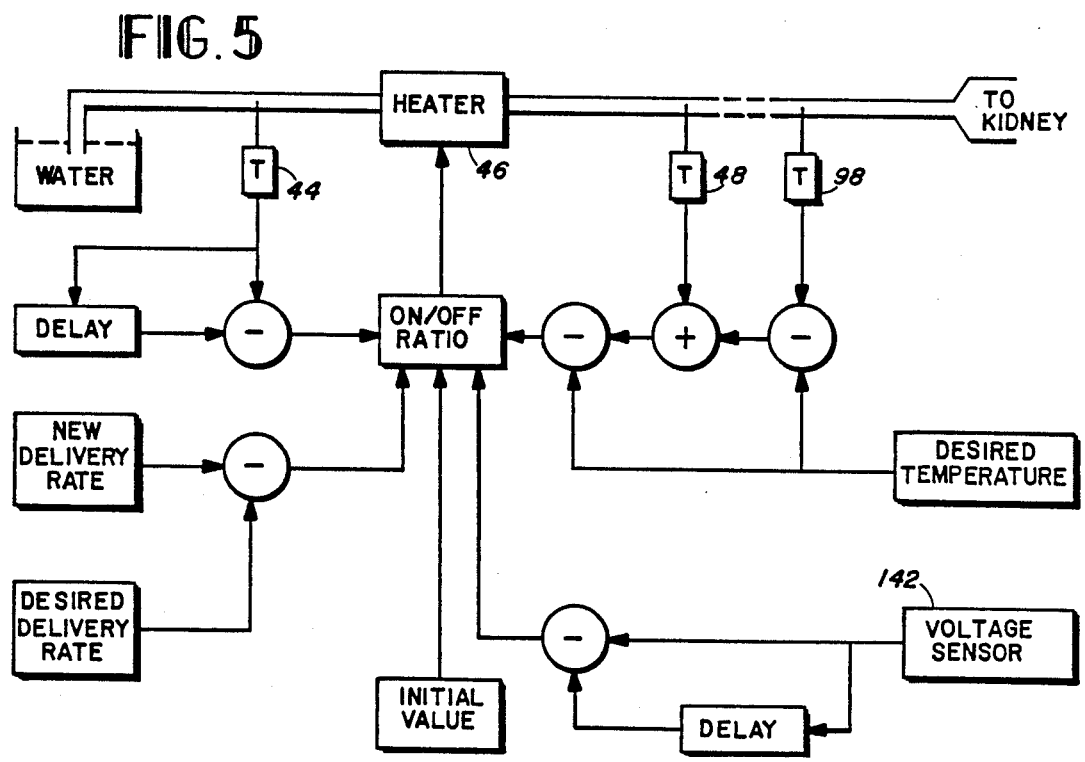
FIG. 5 is a block representation of the temperature control circuit of the dialysis machine of FIG. 1.

As shown in FIG. 5, the hydraulic circuit 34 of the dialysis machine 10 includes four primary components which are utilized by the control processor 122 in maintaining control of the temperature of the delivered dialysate: the temperature feedforward sensor 44, the heater 46, the temperature feedback sensor 48 and the dialysate temperature sensor 90. Initially, the on/off ratio of the heater 46 is established in a conventional manner so that the heat output will be approximately enough to heat the water to the desired delivery temperature given the desired delivery rate. Thereafter, the actual delivery temperature as measured by the dialysate temperature sensor 90 is periodically compared against the desired delivery temperature to determine a preliminary delivery temperature error. This delivery temperature error is then added to the temperature of the water flowing out of the heater 46 as measured by the temperature feedback sensor 48, and the resultant sum again compared against teh desired delivery temperature to determine a final delivery temperature error. This final delivery temperature error is then used to adjust the on/off ration of the heater 46. The on/off ratio is also adjusted whenever the operator changes the dialysis delivery rate. In the preferred form, the on/off ratio is adjusted for two additional sources of error: whenever the temperature of the supply water as measured by the temperature feedforward sensor 44 changes between successive readings; and whenever the supply voltage as measured by a supply voltage sensor 142 changes between successive readings. The first of these adjustments anticipates changes in the temperature of the water flowing from the heater 46 before such changes are sensed by the temperature feedback sensor 48, thereby greatly speeding up the response time of the heater control servoloop. the second of these adjustments anticipates changes in the performance of the heater 46, again before the temperature feedback sensor 48 has had a chance to detect such changes, so that the response time of the heater servoloop is correspondingly improved. The latter change also compensates for variations in the output signals provided by the various temperature sensors due to changes in the supply voltage driving such sensors.

Figure 6:
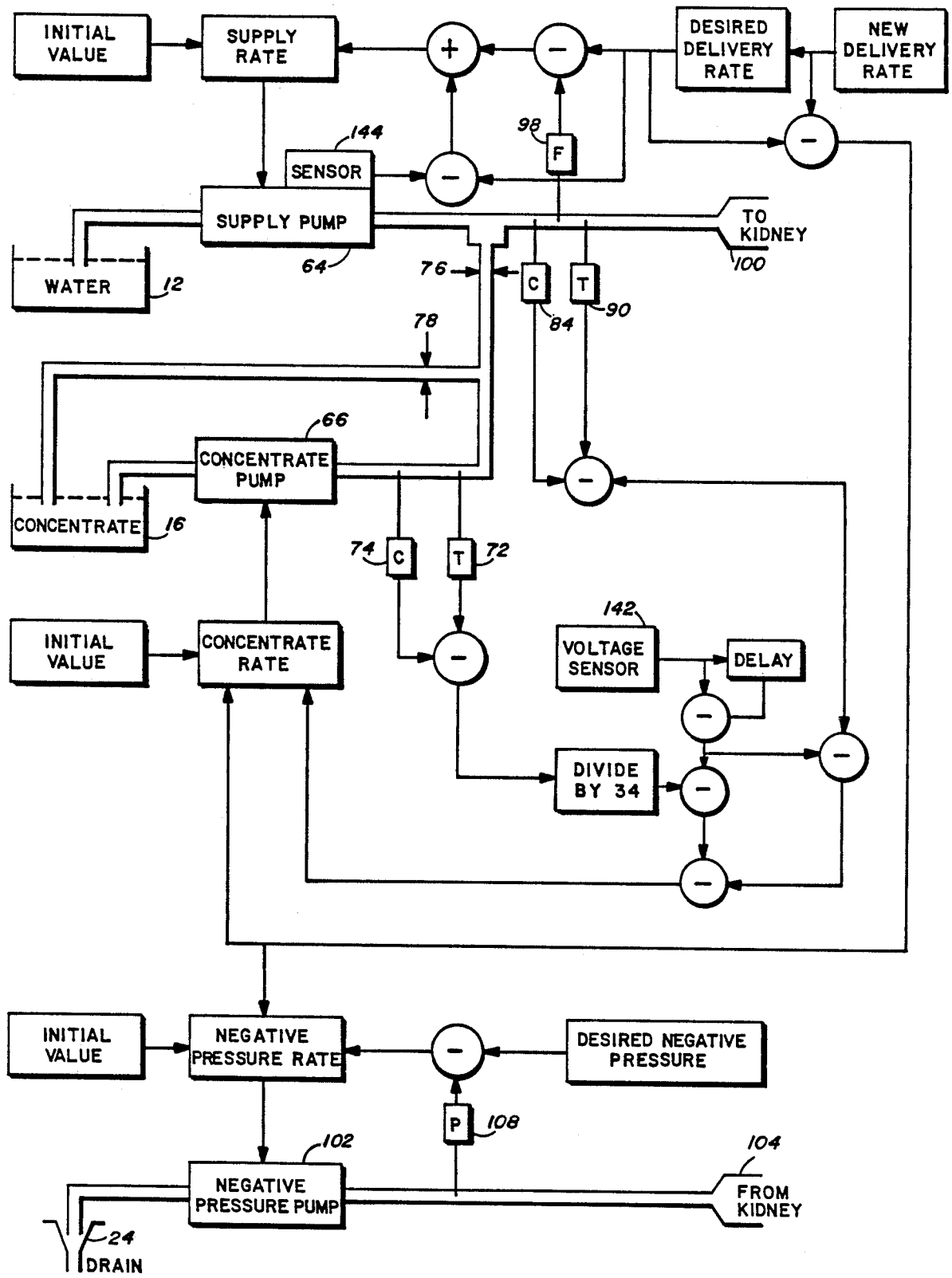
FIG. 6 is a block representation of the flow rate control circuit of the dialysis machine of FIG. 1.

As shown in FIG. 6, the hydraulic circuit 34 of the dialysis machine 10 includes a number of components which are utilized by the control processor 122 in maintaining control of the concentration of the delivered dialysate: the supply and concentrate pumps 64 and 66, respectively; the divider network of injection and return orifices 76 and 78, respectively; the concentrate temperature sensor 72 and the concentrate conductivity cell 74; and the dialysate conductivity cell 84 and the dialysate temperature sensor 90. Initially, the water supply rate is established in a conventional manner so that the heated water being provided by the water supply pump 64 will be approximately enough, when added to a appropriate quantity of concentrate, to provide the dialysate to the artificial kidney 18 at the desired delivery rate. Thereafter, the water supply rate will be adjusted if the actual performance of the water supply pump 64 as measured by a pump speed sensor 144 deviates from the desired flow rate.

Initially, the concentrate supply rate is established to be the same as the water supply rate. Thereafter, the concentrate supply rate is adjusted periodically to compensate for deviations in the conductivity of the delivered dialysate as measured by the dialysate conductivity cell 84 from the proper conductivity, with the conductivity measurement being corrected by the dialysate temperature measurement made simultaneously by the dialysate temperature sensor 90. The concentrate supply rate is also adjusted whenever the opeator changes the dialysate delivery rate. In the preferred form, the concentrate supply rate is adjusted for two additional sources of error: whenever the conductivity of the concentrate as measured by teh concentrate conductivity cell 74 (corrected by the concentrate temperature measurement made simultaneously by the temperature sensor 72) deviates from the desired 34-to-1 ratio relative to the temperature-corrected conductivity of the dialysate; anad whenever the supply voltage as measured by the supply voltage sensor 142 changes between successive readings. The first of these adjustments anticipates changes in the conductivity of the dialysate before such changes are sensed by the dialysate conductivity cell 84, thereby greatly speeding up the response time of the concentration control servoloop. The second of these adjustments anticipates changes in the performance of the concentrate supply pump 66, again before the dialysate conductivity cell 84 has had a chance to detect such changes, so that the response time of the concentration control servoloop is correspondingly improved. The latter change also compensates for variations in the output signals provided by the various temperature and conductivity sensors due to changes in the supply voltage driving such sensors.

With respect to the dialysate return function of the dialysis machine 10, the negative pressure pump 102 is initially set to develop a negative pressure sufficient to maintain the computed transmembrane pressure within the artificial kidney 18. Thereafter, the negative pressure rate is adjusted to compensate for any deviation of the actual negative pressure as measured by the negative pressure sensor 108 from the desired negative pressure. The negative pressure rate is also adjusted whenever the operator changes the dialysis delivery rate.

As can be seen in FIGS. 5 and 6, there are six servoloops of the feedback type:

(1) the output of the temperature feedback sensor 48 is used to periodically adjust the on/off ratio of the heater 46;

(2) the output of the temperature sensor 90 is also used to periodically adjust the on/off ratio of the heater 46;

(3) the output of speed sensor 144 is used to periodically adjust the supply rate which drives the supply pump 64;

(4) the output of flow sensor 98 is also used to periodically adjust the supply rate which drives the supply pump 64;

(5) the output of the conductivity cell 84 is used to periodically correct the concentrate rate which drives the concentratae pump 66; and (6) the output of the pressure sensor 108 is used to periodically adjust the negative pressure rate which drives the negative pressure pump 102.

Figure 7:
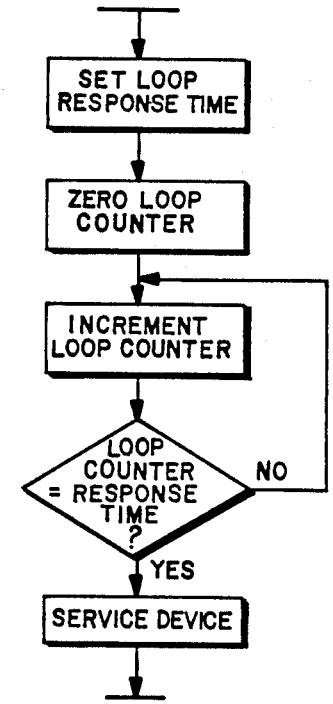
FIG. 7 is a flow diagram of the variable response time service routine periodically executed by the control processor in the control circuit of FIG. 3.

In general, each of these servoloops operates continuously, independently of the other servoloops. However, rather than being limited ot a fixed response period, the periodicity of each of these servoloops is varied in proportion to the current flow rate of the dialysate. In the preferred embodiment, this response period variation is achieved in each of these servoloops generally as shown in FIG. 7.

Initially, a table of loop response periods for each of the servoloops is established in the memory 128, with each value corresponding to the response time which has been empirically determined to be most suitable for a respective flow rate. Thus, for example, the response periode will typically be shorter for the higher flow rates than for the lower flow rates. On the other hand, the response period for the inherently longer servoloops, such as (2) and (4), above, will be longer than the response period of the corresponding shorter servoloops, such as (1) and (3), above, for the same flow rates. Each time through the servoloop, the control processor 122 will determine the instantaneous flow rate using the flow sensor 98 and set the loop response periode for that servoloop in accordance with the corresponding value in the respective table. The control processor 122 will then zero or clear a respective loop counter. Thereafter, the control processor 122 will periodically increment the loop counter for each servoloop.

In the preferred embodiment, the control processor 122 operates on a basic cycle of one/one-hundred-and-twentieth (1/120th) of a second. Each cycle, the control processor 122 reads the output of half of the sensors, so that every one/sixtieth (1/60th) of a second all of the values, including flow rate, in the two (2) current conditions tables are updated. Each basic ccyle, the control processor 122 also increments each of the loop counters. If, after incrementing, a particular loop counter does not equal the loop response period value established in the respective loop response table for the current flow rate, the control processor 122 will simply proceed to the next servoloop. If, after incrementing, a particular loop counter equals the loop response period value established in the respective loop response table for the current flow rate, the control processor 122 will service the corresponding device. The control processor 122 then resets the loop response period for that servoloop in accordance with the corresponding value in the respective table, zeros the loop counter and resumes the incrementing sequence. In this manner, the control processor 122 varies the response time of each of the feedback servoloops in proportion to changes in the flow rate, thereby significantly improving the overall accuracy of the dialysis machine 10.

Figure 8:
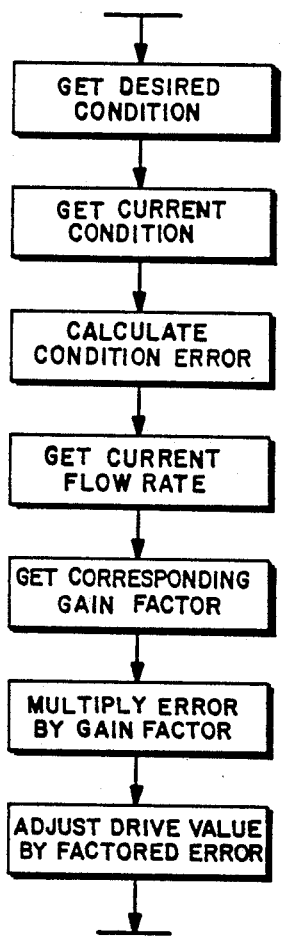
FIG. 8 is a flow diagram of the loop gain correction portion of the service routine of FIG. 7.

In general, the control processor 122 services the heater and pumps by calculating the error, if any, between the current performance of each device against the desired performance, and then adjusting the drive for that device in proportion to the error. However, rather than using the error to directly adjust the drive, the control processor 122 in the preferred embodiment varies the proportionality factor by which the drive is varied in proportion to the current flow rate of the dialysate. This loop gain variation is achieved in each of these servoloops generally as shown in FIG. 8.

As in the case of loop response periods, a table of loop gains for each of the servoloops is initially established in the memory 128, with each value corresponding to the loop gain which has been empirically determined to be most suitable for a respective flow rate. Thus, for example, the loop gain will typically be smaller for the lower flow rates than for the higher flow rates. On the other hand, the loop gains for the servoloop controlling the heater 46 may be quite different from the loop gains of each of the respective servoloops may also be different if necessary to provide the desired accuracy of control.

Each time one of these devices is serviced in a respective servoloop, the control processor 122 will retrieve the appropriate desired and current conditions from the desired conditions and current conditions tables, respectively. The control processor 122 then calculates the "raw" condition error, if any, by subtracting the current from the desired. Using the current flow rate from the current conditions table, the control processor 122 will retrieve the corresponding loop gain factor from the loop gain table for that servoloop. By multiplying the raw condition error by the loop gain factor, the control processor 122 determines the factored error by which the drive value must be adjusted. In this manner, the control processor 122 varies the loop gain of each of the feedback servoloops in proportion to changes in the flow rate, thereby further improving the overall accuracy of the dialysis machine 10.

Figure 9:
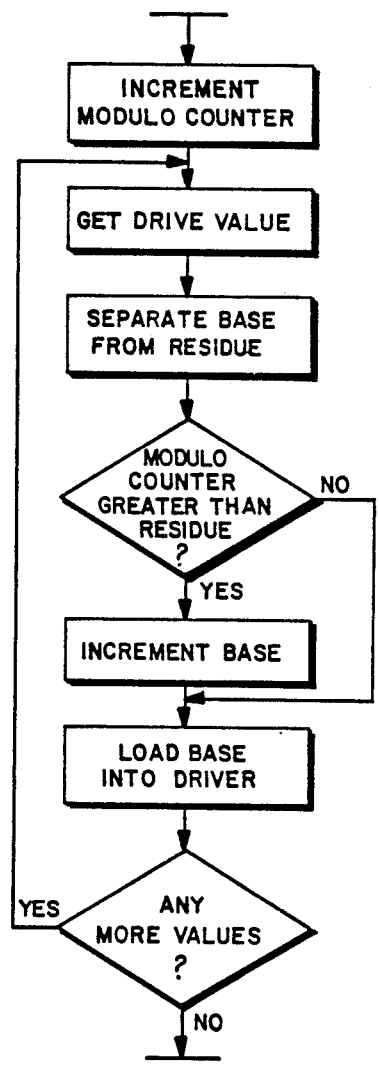
FIG. 9 is a flow diagram of the pump drive adjustment routine periodically executed by the control processor in the control circuit of FIG. 3.
Figure 10:
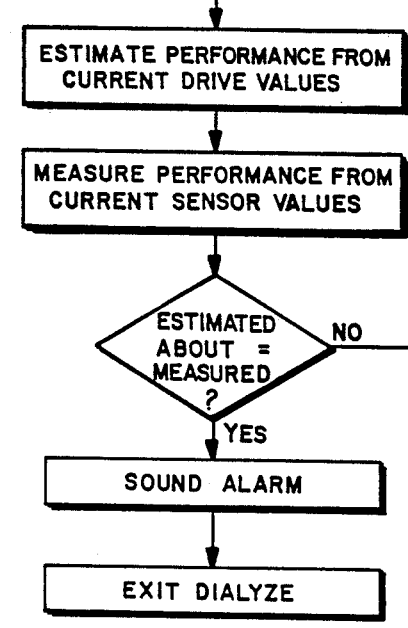
FIG. 10 is a flow diagram of the performance evaluation routine periodically executed by the control processor in the control circuit of FIG. 3.

In general, control processor 122 controls the several valves and the heater 46 by simply turning each on or off at an appropriate time. Accordingly, the drivers 126 for these elements may be relatively simple in construction. In contrast, the control processor 122 controls the several pumps by varying the current applied to each. Since the control processor 122 digitally calculates a drive value for each, the drivers 126 for these elements must include a digital-to-analog (D/A) converter (not shown) of conventional form. However, the cost of D/A converters increases greatly with increasing bits of resolution. For example, an 8-bit D/A costs significantly less than a 10-bit D/A, and very much less than a 12-bit D/A. On the other hand, the 10-bit and 12-bit D/A's allow respectively improved accuracy of control of the flow rates. Thus, it would be highly desirable to provide the accuracy of the higher resolution D/A's without paying the associated price. In the preferred form, the control processor 122 digitally increases the resolution of the D/A's generally as shown in FIG. 9.

Each time one of the pumps is serviced, the control processor 122 calculates a new current drive value to a resolution of say twelve (12) bits (even though the D/A converter in the respective driver 126 may only have an 8-bit resolution) and stores this drive value into a current drive value table in the memory 128. Each basic cycle thereafter, the control processor 122 increments a modulo-16 counter. The control processor 122 then retrieves one of the current drive values and esparates it into a base portion comprising the most significant eight (8) bits and a residue portion comprising the least significant four (4) bits. If the current counter value is less than the residue, the control processor 122 will increment the base and load this "enhanced" base into the D/A converter for the respective driver 126. Otherwise, the control processor 122 will simply load the original base into that D/A converter. The control processor 122 then similarly processes the current drive values for the other pumps. In this manner, the control processor 122 will vary the least significant bit of the bases of each of the current drive values in proportion to the respective residues. In this example, the actual drive values will be enhanced relative to the base values according to the residue bits as follows: six and one-fourth percent (6¼%) of the time if the least significant bit of the residue is "1"; twelve and one-half percent (12½%) of the time if the next most significant bit of the residue is "1"; twenty-five percent (25%) of the time if the next most significant bit of the residue is "1"; and fifty percent (50%) of the time if the most significant bit of the residue is "1". Thus, the control processor 122 digitally "averages" the actual drive values over sixteen (16) basic cycles to provide the desired twelve (12) bits of resolution.

Although the panel processor 120 is primarily responsible for monitoring the current conditions to detect errors, the control processor 122 provides a backup by checking each time the sensors are read that the actual values are not significantly different from the expected values. For example, using a conventional calculation, the control processor 122 can estimate the rotation rate of the supply pump 64 based upon the current drive value, adjusted for the current line voltage. If the output of the sensor 144 indicates a significant deviation from the estimate, the control processor 122 knows that either a conduit is plugged or there is a mechanical-/electrical problem with either the pump 64 or sensor 144. Using another calculation, the control processor 122 can estimate the respective flow rates through the supply pump 64 and concentrate pump 66 based upon the line-voltage-corrected current drive values. If the sum of the two estimated flow rates deviates significantly from the flow rate measured by sensor 98, the control processor 122 knows that a mechanical/electrical problem exists in the flow rate control subsystem. A fault in the conductivity control subsystem is evidenced by a significant different between the estimated conductivity, based upon the estimated flow rates through the supply pump 64 and the concentrate pump 66, and the sensed conductivity as measured by sensor 84. In a similar manner, a fault in the negative pressure subsystem can be detected by comparing the negative pressure as measured by sensor 108 to the estimated negative pressure as calculated from the current drive value for the negative pressure pump 102. With respect to the heater 46, the control processor 122 can estimate the number of calories being added to he supply water based upon the current heater drive value, adjusted for the current line voltage. The control processor 122 can calculate the measured calorie input by multiplying the verified water flow rate times the temperature differential between the input and output water temperatures as measured by sensors 44 and 48, respectively. If there is a significant difference between the estimated and measured values, the control processor 122 knows that an electrical problem exists in the temperature control subsystem.

If any deviation in such operating parameters is detected while the dialysis machine 10 is in the dialyze mode, the control processor 122 responds by immediately returning to the bypass mode and employing an emergency path (not shown) to sound the alarm 124. In the other modes, the control processor 122 simple sounds the alarm 124 and awaits further instructions from the panel processor 120. If for any reason the panel processor 120 fails to resume control, the oepatore can still exercise the option of disconnecting the patient, if present, before manually powering down the dialysis machine 10.

In the preferred embodiment, the panel processor 120 and the control processor 122 each reset respective watchdog timers (not shown) following each exchange of current and desired conditions information. If either processor fails to timely reset the corresponding watchdog, that watchdog will sound the alarm 124. In addition, independently of the control processor 122, the responding watchdog will imediately shut off the blood pump 22 and the infusion pump 26, and force the bypass valve 94 to the bypass postion. In this manner, a failure of one or both processors 120-122 is prevented from harming the patient.

What is claimed is:

1. In a dialysis machine comprising:
   pump means for supplying dialysate to an artificial kidney at a rate proportional to an analog supply rate signal; and
   flow rate control means for providing the analog supply rate signal to the pump means, the analog supply rate signal having a value proportional to the value of a digital flow rate signal, the digital flow rate signal having a first predetermined number of bits of resolution;
   the improvement comprising:
   resolution enhancement means, responsive to a digital flow rate control signal having a second predetermined number of bits of resolution at least one bit greater than said first predetermined number of bits of resolution, for varying the value of the least significant bit of said digital flow rate signal during a selected resolution period in proportion to the value of the least significant bit of said digital flow rate control signal.

2. The dialysis machine of claim 1 wherein the pump means comprise:
   water pump means for supplying water at a rate proportional to an analog water supply rate signal;
   concentrate pump means for supplying dialysate concentrate at a rate proportional to an analog concentrate supply rate signal; and
   mixing means for supplying the dialysate to the artificial kidney by mixing the water supplied to the water pump means with the concentrate supplied by the concentrate pump means; and
   wherein the flow rate control means comprise:
   water flor water control means for providing the analog water supply rate signal to the water pump means, the analog water flow rate signal having a value proportional to the value of a digital water flow rate signal, the digital water flow rate signal having said first predetermined number of bits of resolution; and
   concentrate flow rate control means for providing the analog concentrate supply rate signal to the concentrate pump means, the analog concentrate supply rate signal having a value proportional to the value of a digital concentrate flow rate signal having said first predetermined number of bits of resolution;
   the resolution enhancement menas comprising:
   a first resolution enhancement portion, responsive to a digital water flow rate control signal having said second predetermined number of bits of resolution, for varying the value of the lest significant bit of said digital water flow rate signal during said resolution period in proportion to the value of the least significant bit of said digital water flow rate control signal; and
   a second resolution enhancement portion, responsive to a digital concentrate flow rate control signal having said second predetermined number of bits of resolution, for varying the value of the least significant bit of said digital concentrate flow rate signal during said resolution period in proportion to the value of the least significant bit of said digital concentrate flow rate control signal.

3. The dialysis machine of claim 2 further comprising:
   negative prssure means for developing in the artificial kidney a negative pressure proportional to a negative pressure drive signal; and
   negative pressure control means for providing the negative pressure drive signal to the negative pressure means, the negative pressure control signal having a value proportional to the value of a digital negative pressure drive signal having said first predetermined number of bits of resolution;
   the resolution enhancement means also being responsive to a digital negative pressure drive control signal having said second predetermined number of bits of resolution, and also varying the value of the least significant bit of said digitial negative pressure drive signal during said resolution period in proportion to the value of the least significant bit of said digital negative pressure drive control signal.

4. The dialysis machine of claim 3 wherein the second predetermined number of bits of resolution is greater than said first predetermined number of bits of resolution by a plurality of less significant bits, the resolution enhancement means varying the value of the least significant bit of the digital negative pressure drive signal during said selected resolution period in proportion to the combined binary value of said plurality of less significant bits of said digital negative pressure drive control signal.

5. The dialysis machine of claim 2 wherein the second predetermined number of bits of resolution is greater than said first predetermined number of bits of resolution by a plurality of less significant bits, the first resolution enhancement portion varying the value of the least significant bit of the digital water flow rate signal during said selected resolution period in proportion to the combined binary value of said plurality of less significant bits of said digital water flow rate control signal and the second resolution enhancement portion varying the value of the least significant bit of the digital concentrate flow rate signal during said selected resolution period in proportion to the combined binary value of said plurality of less significant bits of said digital concentrate flow rate control signal.

6. The dialysis machine of claim 1 further comprising:
   negative pressure means for developing in the artificial kidney a negative pressure proportional to a negative pressure drive signal; and
   negative pressure control means for providing the negative pressure drive signal to the negative pressure means, the negative pressure control signal having a value proportional to the value of a digital negative pressure drive signal having said first predetermined number of bits of resolution;
   the resolution enhancement means also being responsive to a digital negative pressure dirve control signal having said second predetermined number of bits of resolution, and also varying the value of the least significant bit of said digital negative pressure drive signal during said resolution period in proportion to the value of the least significant bit of said digital negative pressure drive control signal.

7. The dialysis machine of claim 6 wherein the second predetermined number of bits of resolution is greater than said first predetermined number of bits of resolution by a plurality of less significant bits, the resolution enhancement means varying the value of the least significant bit of the digital negative pressure drive signal during said selected resolution period in proportion to the combined binary value of said plurality of less significant bits of said digital negative pressure drive control signal.

8. The dialysis machine of claim 1 wherein the second predetermined number of bits of resolution is greater than said first predetermined number of bits of resolution by a plurality of less significant bits, the resolution enhancement means varying the value of the least significant bit of the digital flow rate signal during said selected resolution period in proportion to the combined binary value of said plurality of less significant bits of said digital flow rate control signal.

* * * * *